(12) United States Patent
Arasaki et al.

(10) Patent No.: US 12,156,798 B2
(45) Date of Patent: Dec. 3, 2024

(54) ABSORBENT BODY AND SANITARY MATERIAL PRODUCT

(71) Applicant: Toray Industries, Inc., Tokyo (JP)

(72) Inventors: Moriaki Arasaki, Otsu (JP); Katsuhiro Minomo, Otsu (JP); Takashi Oi, Otsu (JP)

(73) Assignee: Toray Industries, Inc., Tokyo (JP)

( * ) Notice: Subject to any disclaimer, the term of this patent is extended or adjusted under 35 U.S.C. 154(b) by 388 days.

(21) Appl. No.: 17/780,601

(22) PCT Filed: Dec. 4, 2020

(86) PCT No.: PCT/JP2020/045181
§ 371 (c)(1),
(2) Date: May 27, 2022

(87) PCT Pub. No.: WO2021/112212
PCT Pub. Date: Jun. 10, 2021

(65) Prior Publication Data
US 2022/0296439 A1   Sep. 22, 2022

(30) Foreign Application Priority Data
Dec. 4, 2019 (JP) ................... 2019-219270

(51) Int. Cl.
*A61F 13/535* (2006.01)
*A61F 13/534* (2006.01)
*A61F 13/537* (2006.01)

(52) U.S. Cl.
CPC ...... *A61F 13/535* (2013.01); *A61F 13/53418* (2013.01); *A61F 2013/53463* (2013.01); *A61F 13/537* (2013.01)

(58) Field of Classification Search
CPC .............. A61F 13/535; A61F 13/537; A61F 13/53418; A61F 2013/53463
See application file for complete search history.

(56) References Cited

U.S. PATENT DOCUMENTS

| 5,554,243 A * | 9/1996 | Igaue ............. A61F 13/531 156/324 |
| 5,665,083 A * | 9/1997 | Igaue ............. A61F 13/531 428/137 |

(Continued)

FOREIGN PATENT DOCUMENTS

| JP | 06190003 A | 7/1994 |
| JP | 0724007 A | 1/1995 |

(Continued)

OTHER PUBLICATIONS

Extended European Search Report for Application No. 20897335.4, dated Oct. 16, 2023, 7 pages.

(Continued)

*Primary Examiner* — Guy K Townsend
(74) *Attorney, Agent, or Firm* — Buchanan Ingersoll & Rooney PC

(57) ABSTRACT

Provided is an absorbent article that has an excellent capability of quickly absorbing a large amount of urine and the like, while preventing loss of the absorbing polymers to the outside of the absorbent article where the absorbent article comprises a first nonwoven fabric and a second nonwoven fabric between which a water-absorbing polymer group is placed, in which the surface of the first nonwoven fabric on the side of the water-absorbing polymer group has openings.

5 Claims, 6 Drawing Sheets

(56) References Cited

U.S. PATENT DOCUMENTS

| | | | | |
|---|---|---|---|---|
| 5,713,881 | A * | 2/1998 | Rezai | A61F 13/15707 604/382 |
| 6,245,051 | B1 * | 6/2001 | Zenker | A61F 13/5376 604/385.23 |
| 6,437,214 | B1 * | 8/2002 | Everett | A61F 13/5376 604/378 |
| 2007/0043330 | A1 * | 2/2007 | Lankhof | A61F 13/51394 604/378 |
| 2007/0167096 | A1 * | 7/2007 | Scott | A61F 13/15203 442/352 |
| 2009/0137975 | A1 * | 5/2009 | Kohira | D04H 3/11 604/385.01 |
| 2013/0046263 | A1 * | 2/2013 | Fukudome | B32B 5/022 604/375 |
| 2013/0331806 | A1 * | 12/2013 | Rosati | A61F 13/53743 604/366 |
| 2014/0005622 | A1 * | 1/2014 | Wirtz | A61F 13/539 604/366 |
| 2014/0005623 | A1 * | 1/2014 | Wirtz | A61F 13/53418 604/366 |
| 2014/0163500 | A1 * | 6/2014 | Roe | A61F 13/49001 604/374 |
| 2014/0163501 | A1 * | 6/2014 | Ehrnsperger | A61F 13/539 604/374 |
| 2014/0163506 | A1 * | 6/2014 | Roe | A61F 13/535 604/378 |
| 2014/0163511 | A1 * | 6/2014 | Roe | A61F 13/532 604/385.101 |
| 2014/0303582 | A1 * | 10/2014 | Wright | A61F 13/15658 156/60 |
| 2015/0005727 | A1 * | 1/2015 | Matsushita | A61L 15/26 442/382 |
| 2015/0065976 | A1 * | 3/2015 | Roe | A61F 13/42 604/374 |
| 2015/0080821 | A1 * | 3/2015 | Peri | C08J 3/245 604/385.01 |
| 2016/0270982 | A1 * | 9/2016 | Raycheck | A61F 13/55105 |
| 2016/0354260 | A1 * | 12/2016 | Roe | A61F 13/532 |
| 2017/0156947 | A1 * | 6/2017 | Esquerra | A61F 13/496 |
| 2017/0281425 | A1 * | 10/2017 | Herfert | A61F 13/535 |
| 2017/0312149 | A1 * | 11/2017 | Bianchi | A61L 15/28 |
| 2019/0192354 | A1 * | 6/2019 | Bewick-Sonntag | A61F 13/47 |
| 2021/0169709 | A1 * | 6/2021 | Bauer | A61L 15/60 |

FOREIGN PATENT DOCUMENTS

| | | |
|---|---|---|
| JP | 11350322 A | 12/1999 |
| JP | 2010148751 A | 7/2010 |
| JP | 2014068856 A | 4/2014 |
| JP | 2015066027 A | 4/2015 |
| WO | 2013099635 A1 | 7/2013 |

OTHER PUBLICATIONS

International Search Report and Written Opinion for International Application No. PCT/JP2020/045181, dated Feb. 22, 2021, 6 pages.

* cited by examiner

ABSORBENT BODY AND SANITARY MATERIAL PRODUCT

CROSS REFERENCE TO RELATED APPLICATIONS

This is the U.S. National Phase application of PCT/JP2020/045181, filed Dec. 4, 2020 which claims priority to Japanese Patent Application No. 2019-219270, filed Dec. 4, 2019 the disclosures of these applications being incorporated herein by reference in their entireties for all purposes.

FIELD OF THE INVENTION

The present invention relates to absorbent articles.

BACKGROUND OF THE INVENTION

Sanitary material products such as paper diapers and napkins include a sheet absorbent article that absorbs and retains a water-based liquid such as urine or menstrual blood (hereinafter, may be referred to as urine or the like), a front side sheet placed on the one side of the absorbent article, and a back side sheet placed on the other side of the absorbent article. The front side sheet is permeable to urine or the like, while the back side sheet is leak-proof to urine or the like. The absorbent article has a structure in which a mixture of pulp fibers and water-absorbing polymers is wrapped by a core wrap. As used herein, the term "core wrap" means a nonwoven fabric or tissue paper.

An absorbent article, a front side sheet, and a back side sheet in a sanitary material product are positioned in the order, from closest to the wearer, of the front side sheet, the absorbent article, and the back side sheet when the sanitary material product is worn.

In recent years, with the spread of sanitary material products such as paper diapers and napkins, sanitary material products are required to have the ability to quickly absorb a large amount of urine and the like.

The following sanitary material products are known to be designed for rapid absorption of a large amount of urine and the like.

Patent Literature 1 discloses a sanitary material product comprising an absorbent article including two hydrophilic nonwoven fabrics sandwiching water-absorbing polymers. Patent Literature 1 also discloses that the upper nonwoven fabric of the two nonwoven fabrics (i.e., the nonwoven fabric, of the two nonwoven fabrics, positioned on the wearer side during wearing the sanitary material product) is an air through nonwoven fabric that is excellent in water permeability. In general, air through nonwoven fabrics are nonwoven fabrics that are bulky and have high porosity. Thus, since the air through nonwoven fabric described in Prior Art 1 is also bulky and has high porosity, the upper nonwoven fabric of two nonwoven fabrics included in the sanitary material product described in Patent Literature 1 considered to exhibit good water permeability.

PATENT LITERATURE

Patent Literature 1: WO 2013/099635

SUMMARY OF THE INVENTION

However, the capability of quickly absorbing a large amount of urine and the like of the absorbent article included in the sanitary material product disclosed in Patent Literature 1 may be insufficient. In addition, further improvement of the capability described above is considered to require smaller particle diameter of the water-absorbing polymer contained in the absorbent article included in the sanitary material product and larger specific surface area of the water-absorbing polymer. Unfortunately, in this case, the absorbing polymer passes through the two nonwoven fabrics sandwiching the absorbing polymer in the absorbent article and the core wrap wrapping the absorbing polymer in the absorbent article, so that the water-absorbing polymer drops out of the absorbent article.

Thus, in view of the aforementioned problems, an object of the present invention is to provide an absorbent article that has an excellent capability of quickly absorbing a large amount of urine and the like, while preventing loss of the absorbing polymers to the outside of the absorbent article.

To solve the above problems, the present invention includes the followings:

(1) An absorbent article comprising a first nonwoven fabric and a second nonwoven fabric that sandwich a water-absorbing polymer group,
  wherein the surface of the first nonwoven fabric on the side of the water-absorbing polymer group has openings,
  wherein the 90% diameter in the diameter distribution of the openings is 10 μm or more and 130 μm or less,
  wherein the difference between the 90% diameter and the 10% diameter in the diameter distribution of the openings is 100 μm or less;
  wherein the surface of the first nonwoven fabric on the opposite side of the water-absorbing polymer group has openings,
  wherein the porosity of the openings is 25% or more and 50% or less;
  wherein the water holding rate of the first nonwoven fabric is 1000 mass % or more;
  wherein at least one surface of the second nonwoven fabric has openings,
  wherein the 90% diameter in the diameter distribution of the openings is 10 μm or more and 130 μm or less,
  wherein the difference between the 90% diameter and the 10% diameter in the diameter distribution of the openings is 100 μm or less;
  wherein the water-absorbing polymer constituting the water-absorbing polymer group is particulate; and
  wherein the particle diameter of the water-absorbing polymer is more than 106 μm and 1000 μm or less.

(2) The absorbent article according to (1),
  wherein the water-absorbing polymer group comprises two layers of water-absorbing polymer groups; and
  wherein the absorbent article further comprises a third nonwoven fabric sandwiched between the two layers of water-absorbing polymer groups.

(3) The absorbent article according to (1) or (2),
  wherein the first nonwoven fabric and the second nonwoven fabric are connected together to form a core wrap sheet.

(4) The absorbent article according to any one of (1) to (3),
  wherein the particle diameter of the water-absorbing polymer is 300 μm or less.

(5) A sanitary material product, comprising an absorbent article according to any one of (1) to (4).

According to the present invention, an absorbent article can be provided, comprising a small-size polymer placed between nonwoven fabrics that have openings with appropriate pore diameters and pore diameter distributions, whereby the absorbent article has an excellent capability of quickly absorbing a large amount of urine and the like, while preventing loss of the absorbing polymers to the outside of the absorbent article.

DETAILED DESCRIPTION OF EMBODIMENTS OF THE INVENTION

Figure 1:
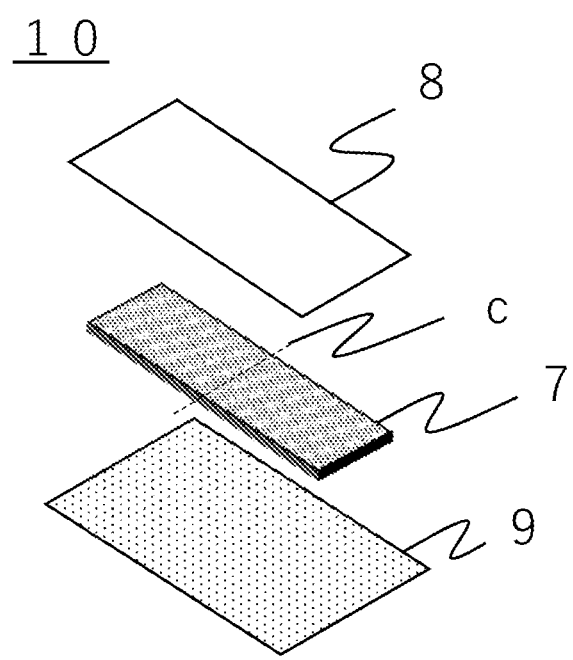
FIG. 1 is a schematic view of an embodiment of a sanitary material product using an absorbent article of the present invention. The line c in the figure indicates the direction corresponding to the cross section in FIGS. 2 to 6.

The present invention will be described in detail below. As used herein, the term "or more" means being the same as or larger than the value shown. The term "or less" means being the same as or smaller than the value shown.
(First Nonwoven Fabric)

First, a first nonwoven fabric included in the absorbent article of the present invention will be described.

Preferably, the first nonwoven fabric comprises 60 mass % or more of a fiber with a standard moisture regain of 8% or more relative to the entire first nonwoven fabric. Such a fiber with a standard moisture regain of 8% or more can be considered as a hydrophilic fiber. The hydrophilicity of this fiber makes it easy to efficiently increase the water holding rate of the first nonwoven fabric, specifically to a range of 1000% or more. The standard moisture regains of short fibers are described in Journal of the Japan Research Association for textile end-uses, 32(3), pages 88-96 (1991).

Specific examples of a fiber with a standard moisture regain of 8% or more include wool fibers, silk fibers, and cellulose fibers, such as cotton fibers, hemp fibers, and rayon fibers. Among these fibers, cellulose fibers, which have an absorbent article excellent in storage stability against insect damage and the like, are preferable. Among cellulose fibers, rayon fibers have high moisture content, 10% or more as a standard moisture regain, which makes it easy to achieve a high water holding rate value for first nonwoven fabric.

Specific examples of the first nonwoven fabric include thermal bond nonwoven fabrics, spunbonded nonwoven fabrics, and spun lace nonwoven fabrics. Among them, the first nonwoven fabric is preferably spun lace nonwoven fabric because it can be made into nonwoven fabric without a binder even when using a cellulose fiber as a fiber constituting the first nonwoven fabric.

In addition, the first nonwoven fabric is preferably laminated nonwoven fabric obtained by laminating and combining two or more layers. In this case, the strength, fineness, and basis weight of the single fibers constituting a layer having one surface of the first nonwoven fabric and a layer having the other surface of the first nonwoven fabric can be adjusted to effectively make the diameter distribution of the openings in the surfaces, specifically the 90% diameter, the 10% diameter, and the difference therebetween, as well as the tactile feel and the like, be within the ranges described below.

When the first nonwoven fabric is laminated nonwoven fabric, it is preferred that the layer (hereinafter, also referred to as "first a layer") having the surface on the side of the water-absorbing polymer group (hereinafter, also referred to as "first a surface") comprises a short fiber including a short fiber with a single fiber strength of 0.1 N or less, and comprises 90 mass % or more of the short fiber with a single fiber strength of 0.1 N or less relative to the entire first a layer. The fiber diameter of the short fiber with a single fiber strength of 0.1 N or less in the first a layer is preferably 15 μm or less, and more preferably 10 μm or less. When the first a layer contains 90 mass % or more, more preferably 95 mass % or more of a short fiber with the single fiber strength as described above and the fiber diameter as described above, the force of pressing and crushing short fibers in the planar direction, such as water jet or calendering, during the manufacturing of the first nonwoven fabric can easily make the fiber axis of the entire short fibers constituting the layer comprising the first a surface oriented in the planar direction and make the diameters of openings formed among the fibers smaller. This effectively makes it easy to allow the 90% diameter in the diameter distribution of the openings contained in the first a surface to be 10 μm or more and 130 μm or less, and the difference between the 90% diameter and the 10% diameter in the diameter distribution to be 100 μm or less. The amount of the short fiber with a single fiber strength of 0.1 N or less contained in the first a layer relative to the entire layer is 100 mass % or less considering the definition, and its fiber diameter is preferably 5 μm or less from the viewpoint of the easy passage in a carding machine as described below.

The type of the short fiber with a single fiber strength of 0.1 N or less contained in the first a layer is not particularly limited as long as it satisfies the properties described above, and is preferably cellulose short fiber from the viewpoint of allowing the water holding capacity of the first nonwoven fabric to be 1000% or more. Especially, the short fiber is preferably a rayon short fiber with a standard moisture regain of 10% or more.

When the first nonwoven fabric is laminated nonwoven fabric, it is preferred that the layer (hereinafter, also referred to as "first b layer") having the surface on the opposite side of the water-absorbing polymer group (hereinafter, also referred to as "first b surface") comprises a short fiber including a short fiber with a single fiber strength of 0.15 N or more, and comprises 10 mass % or more of the short fiber with a single fiber strength of 0.15 N or more relative to the entire first b layer. When the first b layer contains 10 mass % or more, more preferably 20 mass % or more, still more preferably 30 mass % or more of a short fiber with a single fiber strength of 0.15 N or more, more preferably of 0.2 N or more, repulsion of the short fibers due to their rigidity makes it easy to orient the fiber axis of the entire short fibers constituting the first b layer in the thickness direction even through a step applying a force of pressing and crushing short fibers in the planar direction, such as water jet or calendering, during the manufacturing of the first nonwoven fabric. This makes it easy to effectively allow the porosity of the first b surface to be within a desired range. The upper limit of the single fiber strength of the short fiber is not particularly limited, and is preferably 1.0 N or less because it allows for obtaining a first nonwoven fabric with good tactile feel, and a sanitary material product that is not uncomfortable to wear.

The upper limit of the amount of the short fiber with a single fiber strength of 0.15 N or more contained in the first b layer is not particularly limited, and is preferably 50 mass % or less because it allows for obtaining a sanitary material product that is not uncomfortable to wear.

As used herein, the term "single fiber strength of the short fiber" refers to the maximum load in the load-elongation curve obtained by subjecting a short fiber to a tensile test according to JIS L 1015 (2010) 8.7.1. In addition, the term "short fiber" refers to a fiber with a fiber length ranging from 10 to 100 mm. Preferably, the fiber length of the short fiber is from 20 to 80 mm from the viewpoint of the easy passage in a carding machine described below.

Preferred examples of the short fiber with a single fiber strength of 0.15 N or more contained in the first b layer include polyolefin short fibers such as polyethylene and polypropylene, polyester short fibers such as polyethylene terephthalate, polytrimethylene terephthalate, and polybutylene terephthalate, nylon short fibers, acrylic fibers such as acrylonitrile, and vinylon fibers such as polyvinyl alcohol. Among these short fibers, polyester short fibers are preferable from the viewpoint of their excellent strength and versatility. Furthermore, short fibers composed of polyethylene terephthalate are more preferable.

In addition, the short fiber with a single fiber strength of 0.15 N or more contained in the first b layer is preferably a hollow fiber. Preferably, the porosity of the hollow fiber is 10% or more. When the short fiber is a hollow fiber with a porosity of 10% or more, the bulk of the short fiber itself is increased, so that it is easy to allow the porosity of the openings contained in the first b surface to be within the range described below.

The openings contained in the first a surface show the 90% diameter in the diameter distribution of 10 μm or more and 130 μm or less. As used herein, the term "the 90% diameter in the diameter distribution" refers to the diameter of an opening that is determined by arranging observed openings in order of increasing area of each opening, adding together the areas of the openings, starting with the smallest area, and determining the opening at which the accumulated area is the nearest value to 90% of the total area of the openings. Similarly, the 10% diameter described below refers to the diameter of an opening that is determined by arranging the areas of the openings in order of increasing area, adding together the areas of the openings, starting with the smallest area, and determining the opening at which the accumulated area is the nearest value to 10% of the total area of the openings. The opening diameter of an opening refers to the length of the long axis of an ellipse obtained when the opening is approximated as an ellipse. A 90% diameter of the openings of 130 μm or less, preferably of 100 μm or less, makes it easy to prevent the phenomenon of the water-absorbing polymer slipping through fiber gaps in the nonwoven fabric and dropping out on the first b surface. The 90% diameter of the openings in the first a surface of 10 μm or more, preferably 50 μm or more, allows water-based liquid such as urine permeating the first nonwoven fabric to reach the water-absorbing polymer group, so that excellent absorption properties can be effectively obtained.

The openings contained in the first a surface show a difference between the 90% diameter and the 10% diameter in the diameter distribution of 100 μm or less. The difference between the 90% diameter and the 10% diameter is an index representing the breadth of the diameter distribution. In addition to the 90% diameter of the openings falling withing the range described above, when the difference between the 90% diameter and the 10% diameter of the openings is 100 μm or less, preferably 80 μm or less, or the ratio of openings with extremely small opening diameters and openings with extremely large opening diameters to all openings is small, the first nonwoven fabric shows excellent water permeability, as well as excellent performance in preventing loss of the water-absorbing polymer.

As described later in detail, the 90% diameter, and the difference between the 90% diameter and the 10% diameter can be obtained by converting to binary an image of the surface of a nonwoven fabric obtained by SEM observation using an image analyzing software, and performing particle analysis on the portion corresponding to an opening with considering it as a particle.

The openings contained in the first b surface show a porosity of 25% or more and 50% or less. A porosity of 25% or more, preferably 30% or more, or more preferably 40% or more facilitates quick permeation of water-based liquid in a direction from the first b surface to the first a surface. Thus, in wearing a sanitary material product using the absorbent article of the present invention, the first nonwoven fabric, rather than the second nonwoven fabric and water-absorbing polymers, is positioned on the wearer's side, and further the first b surface is positioned on the wearer's side, whereby it is easy for water-based liquid generated from the wearer to quickly permeates into the first nonwoven fabric, and then be absorbed and held by the water-absorbing polymers. That is, the arrangement allows for excellent absorption properties of the absorbent article. On the other hand, a porosity of 50% or less, or preferably 45% or less allows the first nonwoven fabric to show sufficient rigidity, which can prevent the openings in the first b surface from being deformed and crushed, and the water permeability of the first nonwoven fabric to be deteriorated.

As described later in detail, the porosity in the present invention can be obtained by converting to binary an image of the surface of a nonwoven fabric obtained by SEM observation using an image analyzing software.

Preferably, the basis weight of the first nonwoven fabric is 60 g/m$^2$ or less. When the basis weight of the first nonwoven fabric is 60 g/m$^2$ or less, or more preferably 50 g/m$^2$ or less, water-based liquid easily permeates from the first b surface to the first a surface. On the other hand, the lower limit of the basis weight of the first nonwoven fabric is not particularly limited, it is preferably 20 g/m$^2$ or more because it is further ensured that the water-absorbing polymer can be supported as described below.

The first nonwoven fabric has a water holding rate of 1000% or more. When the water holding rate is 1000% or more, or preferably 1200% or more, the first nonwoven fabric can be considered as having preferred hydrophilicity, and water-based liquid such as urine easily permeates into the absorbent article due to the hydrophilicity of the first nonwoven fabric. Thus, in the case where water-based liquid such as urine is generated from a wearer in a sanitary material product using the absorbent article of the present invention, the water-based liquid easily and quickly permeates into the absorbent article. In the case where water-based liquid such as urine is repeatedly generated from a wearer, the hydrophilicity of the first nonwoven fabric is maintained, and thus the absorbent article's capability of quickly absorbing water-based liquid such as urine is likely to be maintained. On the other hand, the upper limit of the water holding rate is not particularly limited, and it is adequately about 3000% from the viewpoint of application in sanitary material products.

The water holding rate can be obtained by washing a nonwoven fabric with an excess amount of water to wash away hydrophilic components attached to the surface, followed by measurement according to JIS L 1913:2010 6.9.2.

(Second Nonwoven Fabric)

Next, a second nonwoven fabric included in the absorbent article of the present invention will be described. The openings contained in at least one surface, preferably in both surfaces, of the second nonwoven fabric show a 90% diameter in the diameter distribution of 10 μm or more and 130 μm or less. A 90% diameter of the openings of 130 μm or less, preferably of 100 μm or less allows for prevention of the phenomenon of the water-absorbing polymer slipping through fiber gaps in the nonwoven fabric and being lost. When the 90% diameter of the openings is 10 μm or more, more preferably 50 μm or more, excellent gas permeability and prevention of stuffed feeling can be obtained.

Openings that satisfy the 90% diameter as described above in the second nonwoven fabric show a difference between the 90% diameter and the 10% diameter in the diameter distribution of 100 μm or less. When the difference between the 90% diameter and the 10% diameter of the openings is 100 μm or less, preferably 80 μm or less, or the ratio of openings with extremely small opening diameters and openings with extremely large opening diameters to all openings is small, the second nonwoven fabric shows excellent performance in preventing loss of the water-absorbing polymer.

The second nonwoven fabric is not particularly limited as long as it has the structure described above, and may be the same nonwoven fabric as the first nonwoven fabric, or a different nonwoven fabric from the first nonwoven fabric.

(Core Wrap Sheet)

Figure 4:
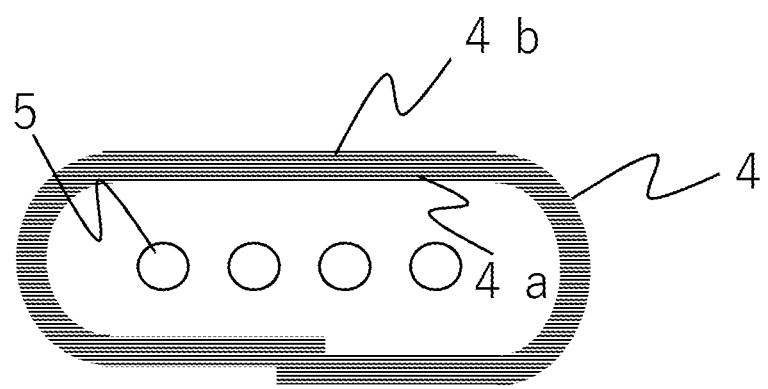
FIG. 4 is a schematic view of a cross section across the line c of an absorbent article in another embodiment of the present invention.

Preferably, the first nonwoven fabric and the second nonwoven fabric may be a core wrap sheet connected together. The term "core wrap sheet" refers to a material that serves to wrap and hold the water-absorbing polymer. In the case where the shape of the absorbent article is a substantially rectangular sheet, a core wrap sheet material with a shape of substantially rectangular sheet is folded so that its two sides, for example, approximately overlap at the position of the line connecting the midpoints of the two short sides of the absorbent article, and water-absorbing polymers are held inside of the core wrap sheet. In such a structure after the core wrap sheet material is folded, or after the absorbent article is formed, the both ends of the long sides of the substantially rectangular sheet absorbent article are closed by the core wrap sheet. Closure of the both ends of the long sides of the absorbent article by the core wrap sheet can provide effects of preventing the phenomenon of water-absorbing polymers dropping out from the edges of the absorbent article, and of preventing the phenomenon of water-based liquid such as urine permeating into the absorbent article leaking out from the edges of the absorbent article. In the structure showed in FIG. 4, a core wrap sheet 4 encloses a water-absorbing polymer group 5.

(Water-Absorbing Polymer Group)

Next, a water-absorbing polymer group included in the absorbent article of the present invention will be described. The water-absorbing polymer group is an aggregate of particulate water-absorbing polymers. The water-absorbing polymer may be, for example, starch, a cross-linked carboxymethylated cellulose, an acrylic acid or alkali metal acrylate polymer or a copolymer thereof, polyacrylate such as sodium polyacrylate or a polyacrylate graft polymer. Among them, sodium polyacrylate is preferable.

Preferably, the water-absorbing polymer has a physiologic saline absorption ratio per gram of the water-absorbing polymer of from 25 to 50 times, and a physiologic saline absorption speed per gram of the water-absorbing polymer or 45 seconds or less, from the viewpoint that the absorbent article shows better absorption properties. Here, the saline solution absorption ratio of the water-absorbing polymer is measured by the tea-bag method specified in JIS K7223 (1996), and the physiologic saline absorption rate of the water-absorbing polymer is measured by the Vortex method specified in JIS K7224 (1996).

The particle diameter of the water-absorbing polymer forming the water-absorbing polymer group is more than 106 μm and 1000 μm or less. When the particle diameter of the water-absorbing polymer is 1000 μm or less, preferably 500 μm or less, more preferably 425 μm or less, still more preferably 300 μm or less, still more preferably 212 μm or less, discomfort due to unevenness felt by the wearer when wearing a sanitary material product comprising the absorbent article of the present invention can be reduced. In addition, such a particle diameter provides a large specific surface area for each water-absorbing polymer, facilitating quick absorption and retention of water-based liquid such as urine by the water-absorbing polymer. On the other hand, when the particle diameter of the water-absorbing polymer is more than 106 μm, it is possible to prevent the water-absorbing polymer from slipping through gaps among fibers constituting the first nonwoven fabric or second nonwoven fabric and dropping out of the absorbent article from the inside to the outside of the absorbent article.

The particle diameter of the water-absorbing polymer will be defined by the size of the sieve used to classify the water-absorbing polymer. As a more specific example, when a sieve with an aperture of 1000 μm is placed on top of a sieve with an aperture of 106 μm, and water-absorbing polymers are placed on the sieve with an aperture of 1000 μm and shaken for 10 minutes, the particle diameter of the water-absorbing polymer remaining on the sieve with an aperture of 106 μm will be more than 106 μm and 1000 μm or less. When a sieve with an aperture of 300 μm is placed on top of a sieve with an aperture of 106 and water-absorbing polymers are placed on the sieve with an aperture of 300 μm and shaken for 10 minutes, the particle diameter of the water-absorbing polymer remaining on the sieve with an aperture of 106 μm will be more than 106 μm and 300 μm or less.

The content of the water-absorbing polymer satisfying the particle diameter described above in the water-absorbing polymer group is preferably 90 mass % or more, and particularly preferably 100 mass %, or, each of the water-absorbing polymers satisfies the particle diameter described above.

When a sodium polyacrylate water-absorbing polymer is used as the water-absorbing polymer in the present invention, it can be obtained by separating a component with the particle diameter described above from "SANWET" series manufactured by SDP Global Co., Ltd. or "AQUALIC" series manufactured by Nippon Shokubai Co., Ltd. using a sieve.

In the absorbent article of the present invention, the basis weight of the water-absorbing polymer group is preferably 100 g/m$^2$ or more and 500 g/m$^2$ or less. It is known that when densely packed water-absorbing polymers come into contact with a water-based liquid such as urine, the water-absorbing polymers after absorption and expansion come into contact with each other, causing a "gel block phenomenon" that prevents other water-absorbing polymers without absorption and expansion from coming into contact with a water-based liquid such as urine. However, when the basis weight of the water-absorbing polymer group is within the range described above, the water-absorbing polymer particles are present at appropriate intervals between each other, avoiding the "gel block phenomenon" and facilitating efficient functioning of the water-absorbing polymer. In the case where the water-absorbing polymer group is separated into a first water-absorbing polymer group and a second water-absorbing polymer group as described below, the total of the basis weight of the first water-absorbing polymer group and the basis weight of the second water-absorbing polymer group is considered as the basis weight of the water-absorbing polymer group.

(Third Nonwoven Fabric)

Figure 3:
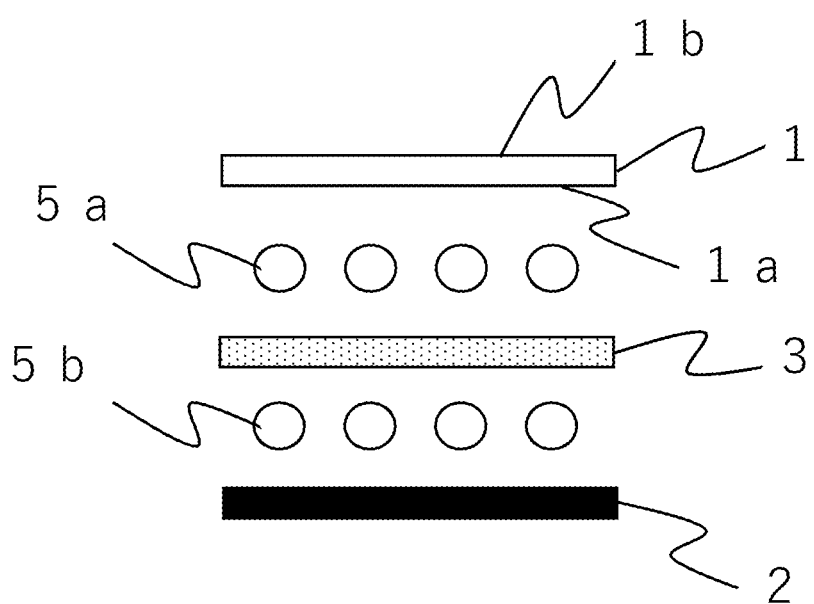
FIG. 3 is a schematic view of a cross section across the line c of the absorbent article of the present invention when using a third nonwoven fabric.
Figure 5:
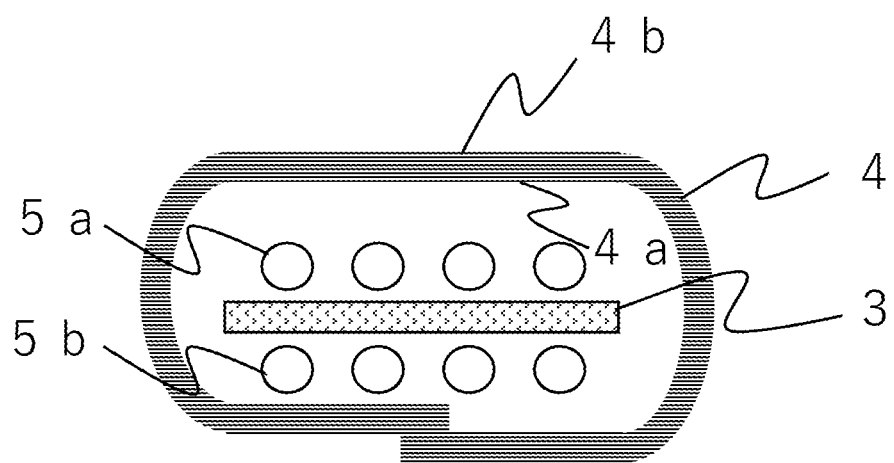
FIG. 5 is a schematic view of a cross section across the line c of the absorbent article in another embodiment of the present invention when using a third nonwoven fabric.

Preferably, the absorbent article of the present invention comprises two layers of water-absorbing polymer groups, between which a third nonwoven fabric is further included. In FIGS. 3 and 5, a third nonwoven fabric (3 in FIGS. 3 and 5) is placed between two layers of water-absorbing polymer groups (5a and 5b in FIGS. 3 and 5). In such a structure, a water-based liquid such as urine permeating into the inside of the absorbent article through the third nonwoven fabric easily diffuses inside of the absorbent article in the planar direction of the third nonwoven fabric, which enables further improved water absorption efficiency of the entire water-absorbing polymer group. Thus, when the absorbent article of the present invention is used in a sanitary material product, the sanitary material product can easily retain a larger amount of a water-based liquid such as urine.

The water absorption height of the third nonwoven fabric in the Byreck-method water absorption test is preferably 30 mm or more, more preferably 100 mm or more, and still more preferably 125 mm or more, from the viewpoint that the role of the third nonwoven fabric is to diffuse water-based liquids such as urine inside the absorbent article.

(Absorbent Article)

Figure 2:
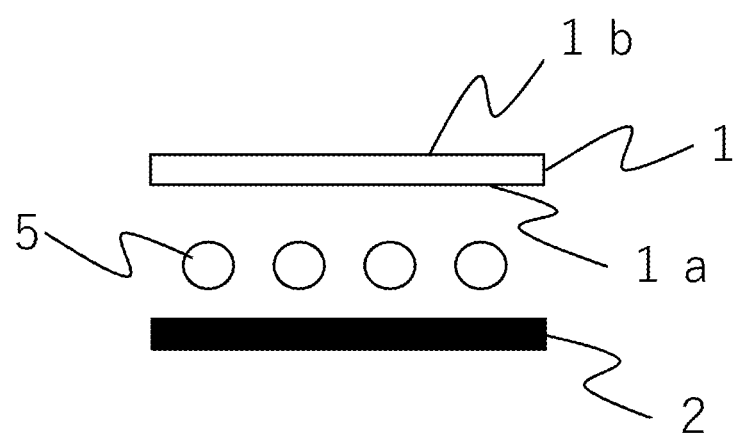
FIG. 2 is a schematic view of a cross section across the line c of the absorbent article of the present invention.

The absorbent article of the present invention comprises the first nonwoven fabric and the second nonwoven fabric, between which the water-absorbing polymer group is placed. The positional relationship of openings and the water-absorbing polymer group in the first nonwoven fabric is as described above. In FIG. 2, a first nonwoven fabric (1 in FIG. 2) and a second nonwoven fabric (2 in FIG. 2) sandwich a water-absorbing polymer group (5 in FIG. 2). In such a structure, when the absorbent article of the present invention is used in a sanitary material product such as diaper, water-based liquids such as urine emitted by the wearer quickly permeate into the absorbent article and are quickly absorbed and retained by the water-absorbing polymer. Thus, sanitary material products that are not uncomfortable to wear and leak less can be obtained.

Preferably, the absorbent article of the present invention is a substantially rectangular sheet, similar to known absorbent articles used in sanitary material products such as diapers.

Preferably, the absorbent article of the present invention has a thickness of 3 mm or less. When the thickness of the absorbent article is 3 mm or less, and when the absorbent article of the present invention is used in a sanitary material product such as diaper, the sanitary material product using the absorbent article of the present invention is likely to be flexible, have less stiffness, and be excellent in wearability. From the reason that the sanitary material product exhibits improved wearability, the absorbent article is preferably thinner, and the thickness of the absorbent article is preferably 2.5 mm or less. In addition, from the reason that the absorbent article exhibits better absorption properties, the thickness of the absorbent article is preferably 1 mm or more. Here, the thickness of the absorbent article refers to that measured according to JIS L1913 (2010) 6.1.1 A.

Figure 6:
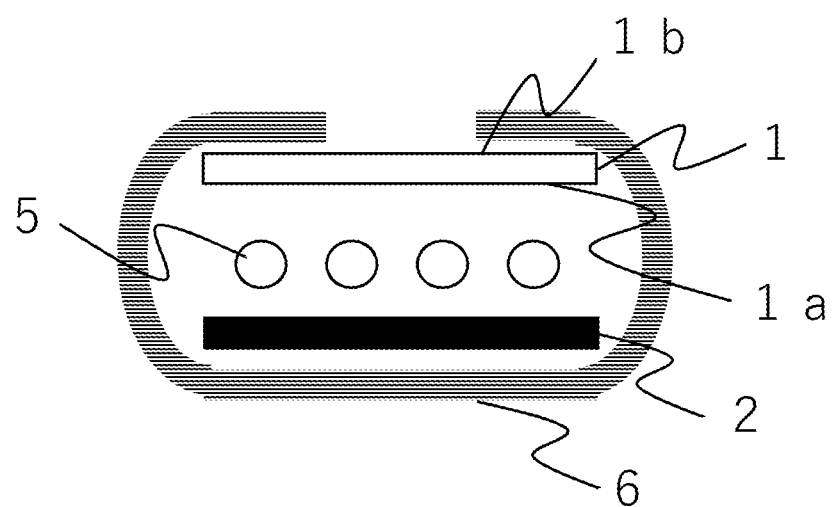
FIG. 6 is a schematic view of a cross section across the line c of an absorbent article in an embodiment of the present invention when using a covering material.

Preferably, the absorbent article of the present invention is also partially covered with a covering material from the viewpoint of transportability during manufacturing of the absorbent article and shape retention properties of the absorbent article itself. A specific example of the absorbent article in a state covered with a covering material is illustrated in FIG. 6. In FIG. 6, the absorbent article has a shape of substantially rectangular sheet. A substantially rectangular sheet covering material 6 used in the absorbent article partially covers the absorbent article by fixation of the two long sides of the substantial rectangle on the first nonwoven fabric. Such a configuration makes it easier to maintain the water-based liquid permeability of the first nonwoven fabric into the absorbent, as well as to provide good transportability during manufacturing of the absorbent article and good shape retention properties of the absorbent article itself, as described above. The covering material is not particularly limited, a nonwoven fabric is preferred from the viewpoint of lightweight properties and air permeability, or a spun-bonded nonwoven fabric with excellent strength properties is preferred in terms of transportability and shape retention properties.

(Method of Manufacturing Absorbent Article)

The method of manufacturing the absorbent article of the present invention will be described in detail, but the absorbent article of the present invention is not limited to those manufactured by the manufacturing methods described below.

A water-absorbing polymer group is held between the first nonwoven fabric and the second nonwoven fabric to obtain an absorbent article. Methods of holding the water-absorbing polymer include a method comprising spraying or spiral-spraying a hot melt adhesive onto a first surface of a first nonwoven fabric, and spraying a water-absorbing polymer thereon to form a water-absorbing polymer group, and then, putting a second nonwoven fabric with similarly the one surface sprayed with a hot melt adhesive on the water-absorbing polymer group so that the hot melt adhesive and the water-absorbing polymer are in contact with each other, and fixing them by applying pressure.

In the case where a third nonwoven fabric is used to separate the water-absorbing polymer group into a first water-absorbing polymer group and a second water-absorbing polymer group, a hot melt adhesive is sprayed or spiral-sprayed onto a first surface of a first nonwoven fabric, onto which a water-absorbing polymer is sprayed to form a first water-absorbing polymer group, and then, a third nonwoven fabric with similarly the one surface sprayed with a hot melt adhesive is put on the first water-absorbing polymer group so that the hot melt adhesive and the first water-absorbing polymer are in contact with each other, followed by fixation by applying pressure, in the same manner as described above. Thereafter, a hot melt adhesive is sprayed onto the other surface of the third nonwoven fabric, onto which a water-absorbing polymer is sprayed to form a second water-absorbing polymer group, and then, a second nonwoven fabric with similarly the one surface sprayed with a hot melt adhesive is put on the first water-absorbing polymer group so that the hot melt adhesive and the first water-absorbing polymer are in contact with each other, followed by fixation by applying pressure.

A styrene hot melt adhesive or an olefin hot melt adhesive that is suitable for use in sanitary material products may be used as a suitable hot melt adhesive.

The amount of the hot melt adhesive sprayed is preferably 0.5 g/m$^2$ or more and 3 g/m$^2$ or less in the interfaces formed between the nonwoven fabrics and the water-absorbing polymer group, from the viewpoint that the water-absorbing polymer is held on the nonwoven fabrics, and from the viewpoint of inhibition of expansion of the water absorbing polymer by the hot melt adhesive.

The method of manufacturing an absorbent article in the case where the first nonwoven fabric and the second nonwoven fabric are connected together and form a core wrap sheet will be described in detail. A water-absorbing polymer group is held on the surface of the core wrap sheet cut into a substantially rectangular sheet shape on the side of the water-absorbing polymer group (the surface corresponding to a first a surface) using a hot melt adhesive. Then, considering a line obtained by connecting the midpoints of a pair of the short sides of the substantially rectangular core wrap sheet as center line, the core wrap sheet is folded so that the vicinities of the two long sides of the substantially rectangular core wrap sheet overlap at the position of the center line, and then the vicinities of the long sides are fixed by applying pressure. In this way, a form in which the water-absorbing polymer group is wrapped by the core wrap sheet is obtained. In the case where a third nonwoven fabric is used, a water-absorbing polymer group is held on the surface of the core wrap sheet cut into a substantially rectangular sheet shape on the side of the water-absorbing polymer group (the surface corresponding to a first a surface) using a hot melt adhesive, and then the third nonwoven fabric with the one surface sprayed with a hot melt adhesive is allowed to cover the water-absorbing polymer group so that the hot melt adhesive and the water-absorbing polymer group is in contact with each other. Thereafter, a hot melt adhesive is sprayed onto the other surface of the third nonwoven fabric, and the core wrap sheet is folded so that two long sides of the core wrap sheet overlap at the position of the center line, followed by fixation by applying pressure.

For efficient production, it is also preferable to manufacture an absorbent article that continues in the longitudinal direction using nonwoven fabrics that continue in the longitudinal direction and cut it to the required length.

(Sanitary Material Product and Manufacturing Method Thereof)

The absorbent article of the present invention can be preferably used in sanitary material products such as paper diapers and napkins. Thus, the sanitary material product of the present invention comprises the absorbent article of the present invention.

The absorbent article of the present invention can be preferably used in sanitary material products. Thus, the sanitary material product of the present invention comprises the absorbent article of the present invention. FIG. 1 shows the sanitary material product of the present invention (10 in FIG. 1) comprising the absorbent article of the present invention (7 in FIG. 1) between a front side sheet (8 in FIG. 1) and a back side sheet (9 in FIG. 1).

The method of manufacturing the sanitary material product of the present invention will be described. After cutting the absorbent article of the present invention to the required length, the absorbent article is sandwiched and held between a front side sheet and a back side sheet that are in a shape of substantially rectangular sheet similar to the cut absorbent article, and have larger areas than the absorbent article after cutting. At this time, the absorbent article is preferably sandwiched so that the first nonwoven fabric is in contact with the front side sheet. The first nonwoven fabric has characteristics that facilitate permeation of water-based liquid such as urine from one surface (first b surface) to the other surface (first a surface). Thus, when the front side sheet is in contact with the first nonwoven fabric, it is likely that a water-based liquid such as urine that have permeated into the front side sheet quickly pass through the first nonwoven fabric, and is absorbed and retained by the water-absorbing polymer. Thus, improved absorption properties of the absorbent article are obtained. In the case where the absorbent article uses a core wrap sheet, the absorbent article is preferably sandwiched by the front side sheet and the back side sheet so that seems in the core wrap sheet are positioned on the back side sheet side to avoid burdening the wearer due to tactile feel. The method for fixing the front side sheet and the absorbent article, the back side sheet and the absorbent article, and the front side sheet and the back side sheet where they are in direct contact with each other may be a method using a hot melt adhesive or a method using a thermal adhesive resin powder.

As the front side sheet used in making the absorbent article of the present invention into a sanitary material product, a nonwoven fabric is preferably used from the viewpoint of improved liquid permeability and tactile feel. For example, a wet nonwoven fabric, a resin bonded dry nonwoven fabric, a thermal bond dry nonwoven fabric, a spunbonded dry nonwoven fabric, a needlepunched dry nonwoven fabric, a water jet punched dry nonwoven paper fabric, a flashspun dry nonwoven fabric, or the like, or a nonwoven fabric manufactured by paper-making methods that allow for uniform basis weight and thickness is preferably used. Among them, a thermal bond dry nonwoven fabric that has excellent tactile feel is preferably used as the front side sheet from the viewpoint that it is positioned in contact with human skin.

As the back side sheet used in making the absorbent article of the present invention into a sanitary material product, it is preferably a laminated sheet of a moisture-permeable and waterproof film and a nonwoven fabric from the viewpoint of allowing water vapor accumulated inside the sanitary material product to escape to the outside and thereby providing comfort to the wearer, and the viewpoint that the waterproof properties and tactile feel can be improved. Examples of the moisture-permeable and waterproof film include porous polyethylene films, moisture-permeable urethane films, and moisture-permeable polyester elastomer films. As the nonwoven fabric described above, the same nonwoven fabric as of the front side sheet can be used, a spunbonded dry nonwoven fabric is preferable from the viewpoint of cost and strength.

Example

The present invention will now be described in more detail with reference to examples, but is not limited to them.

[Methods of Measurement and Evaluation]

(1) Basis Weight of Nonwoven Fabric

The basis weight was measured according to JIS L 1913 (2010) 6.2. Three 25 cm×25 cm test pieces were obtained from a nonwoven fabric. The masses (g) were measured under standard conditions, and the basis weights (g/m²) were determined according to the following formula, and then the average value was calculated.

$$Sm = W/A$$

Sm: basis weight (g/m²)
W: the mass of the test piece (g) under standard conditions
A: the area (m²) of the test piece (2) Water Absorption Height of Nonwoven Fabric in Byreck-Method Water Absorption Test The water absorption height was measured by Byreck method according to JIS L1907 (2010) 7.1.2. Specifically, five 200 mm×25 mm test pieces were taken from a nonwoven fabric. After fixing the test piece on a horizontal bar supported above the surface of the water in a water-filled tank, the horizontal bar was lowered and adjusted so that 20 mm of the bottom of the test piece was immersed in water and then left for 10 minutes. After leaving the test piece, the height to which the water rose by capillary action was measured to 1 mm on a scale, and the average value of five test pieces was obtained.

(3) Content of Fiber Constituting Nonwoven Fabric

The mixture ratio based on corrected mass (the mass ratio of fibers under standard conditions) was measured according to JIS L 1030-1 (2012) "Testing methods for quantitative analysis of fibre mixtures—Part 1: Testing methods for fibre identification", and JIS L 1030-2(2012) "Testing methods for quantitative analysis of fibre mixtures of textiles—Part 2: Testing methods for quantitative analysis of fibre mixtures," and was defined as the content (mass %) of the fiber constituting the nonwoven fabric.

(4) Water Holding Rate of Nonwoven Fabric

The water holding rate of nonwoven fabrics was measured according to JIS L 1913 (2010) 6.9.2. Five 100 mm×100 mm test pieces were prepared, and their masses were measured. Next, 3 L of distilled water was placed in a container with an appropriate size, and then the test pieces were immersed in distilled water at 20° C. for 30 minutes. Thereafter, the test pieces were replaced in 3 L of distilled water prepared separately using tweezers and again immersed for 30 minutes, which operations were repeated twice in total, thereby removing the hydrophilizing agent and the like adhering to the surface of the nonwoven fabric. Next, one end of the test piece was hung with a clip, allowing water to drip down for one minute, and then the mass of the test piece was measured, which was defined as the mass in the water-retaining state. The water holding rate of each of the obtained five test pieces was calculated using the following equation, and the average value from the five test pieces was determined.

$$m = (m2 - m1)/m1$$

m: water holding rate (fold mass)
m1: mass (g) of the test piece under standard conditions
m2: mass (g) of the test piece after being wetted and allowing water to drip down (5) 90% Opening Diameter, Difference between 90% Opening Diameter and 10% Opening Diameter, and Porosity of Openings in Nonwoven Fabric The values were determined by image analysis of the surface image of the nonwoven fabric obtained by scanning electron microscopy. Specifically, the observation was made using a scanning electron microscope (S-3400N manufactured by Hitachi High-Tech Corporation) at a magnification of 70×. The obtained image was read with an image analyzing software ImageJ, and binarized with the upper and lower limit thresholds set to 0. Then, considering openings formed among fibers as particles, openings with an area of 100 μm' or more were subjected to particle analysis. Openings that were in contact with the boundaries of the image were omitted from the analysis. Openings observed by the microscopy were those with the diameter described below of 10 μm or more because of the effect of noise in the image analysis.

The openings obtained by the analysis were arranged in order of increasing area, the areas were added together starting with the smallest area, the opening at which the accumulated area was the nearest value to 10% of the total area of the openings was determined, and the diameter of the opening was defined as 10% diameter. The openings obtained by the analysis were arranged in order of increasing area, the areas were added together starting with the smallest area, the opening at which the accumulated area was the nearest value to 90% of the total area of the openings was determined, and the diameter of the opening was defined as the 90% diameter. Here, when there were two openings at which the accumulated area was the nearest value to 10% of the total area of the openings, the opening diameter of the opening with larger diameter was considered as the 10% diameter. Here, when there were two openings at which the accumulated area was the nearest value to 90% of the total area of the openings, the diameter of the opening with larger diameter was defined as the 90% diameter. The diameter of an opening refers to the length of the long axis of an ellipse obtained when the opening is approximated as an ellipse. The difference between the 90% diameter and the 10% diameter was used as an indication of the width of the particle size distribution.

The porosity was calculated based on the total area of the openings relative to the entire image.

(6) Single Fiber Strength of Short Fiber

The single fiber strength was measured according to JIS L1015 (2010) 8.7.1. A single fiber was loosely stretched and each end of the fiber was attached to paper with an additive, thereby preparing a sample with the paper-attached portions as gripping portions. In this case, the length of the fiber-only portion between the gripping portions was ensured to be 20 mm. The gripping portions of the sample were attached to the grippers of a tensile tester (TENSILON universal testing instrument, model RTG-1210, manufactured by Orientec Co., Ltd.), and pulled at a rate of pull of 10 mm/min with the length of sample between the grippers of 10 mm. The maximum load on the obtained elongation (mm)–load (N) curve was defined as the single fiber strength (N). Measurements were done for 10 samples and the average value was calculated.

(7) Standard Moisture Regain of Short Fiber

When the composition of the short fiber was known, the standard moisture regain of a fiber with the same composition as described in Journal of the Japan Research Association for textile end-uses (1991) 32(3) 88-96 was considered as the standard moisture regain of the short fiber. When the composition of the short fiber was unknown, the composition of the short fiber was determined by the method described in (3) above, and the standard moisture regain of a fiber with the same composition as described in Journal of the Japan Research Association for textile end-uses (1991) 32(3) 88-86 was defined as the standard moisture regain of the short fiber.

(8) Porosity and Fiber Diameter of Short Fiber

The fiber cross section exposed by cutting a short fiber sample from a direction perpendicular to the fiber axis using an ultramicrotome was observed using a scanning electron microscope (S-3400N, manufactured by Hitachi High-Tech Corporation) at a magnification of 500× to 1,500×. When the presence of a space inside the fiber was confirmed in the obtained fiber cross-sectional image, the image was automatically binarized using ImageJ image analyzing software before the area of the fiber component and the area of the space inside the fiber were determined, and the porosity was calculated using the following equation.

$$\text{Porosity (\%)}=[S1/(S1+S2)]\times 100$$

S1: area of fiber portion
S2: area of space inside fiber

The same observation was performed, and the long axis and short axis of the obtained fiber cross sectional image were measured, and their average value was defined as the fiber diameter.

(9) Thickness of Absorbent Article

The thickness of the absorbent article was measured by a method according to JIS L1913 (2010) 6.1.1 A. Specifically, five 50 mm×50 mm test pieces were taken from a nonwoven fabric sample. The thickness was measured after applying a pressure of 0.36 kPa to the test piece for 10 seconds using as thickness measuring instrument (constant pressured thickness measuring instrument, model PG11 J, manufactured by TECLOCK Corporation) under standard conditions. Measurements were done for the five test pieces and the average value was calculated.

(10) Loss of Water-Absorbing Polymer from Absorbent Article

After the absorbent article was shaken in a sieve shaker, the amount of the water-absorbing polymer that dropped out through the nonwoven fabric was measured. Specifically, an absorbent article cut out in a circular shape with a diameter of 75 mm and an area of 44 cm² was placed on a sieve with a diameter of 75 mm and an aperture of 500 The sieve was placed on MVS-1N, a mini sieve shaker manufactured by AS ONE Corporation. After shaking for 5 minutes with a memory setting of 3, the mass (g) of the water-absorbing polymer that dropped out through the lower nonwoven fabric of the absorbent article was measured. Then, the absorbent article placed on the sieve was placed again on the sieve so that the top and bottom were surfaces were switched. After shaking in the same manner, the mass (g) of the water-absorbing polymer that dropped out through the other nonwoven fabric of the absorbent article was measured. Based on the obtained weight of the water-absorbing polymer, the loss was calculated according to the following equation.

$$\text{Loss}(g/m^2)=(n1+n2)\times 10000/44$$

n1: the amount of the water-absorbing polymer that dropped out through one nonwoven fabric of the absorbent article n2: the amount of the water-absorbing polymer that dropped out through the other nonwoven fabric of the absorbent article

(11) Amounts of Backflow, and of Backflow after Repeated Use in Sanitary Material Product A front side sheet, an absorbent article, and a back side sheet were bonded together to form a sanitary material product as a sample. Then, 20 ml of physiologic saline (9% aqueous sodium chloride solution) prepared as a water-based liquid mimicking urine was administered from the front side sheet side of the sample. Five minutes after administration of the physiologic saline, filter paper (qualitative filter paper No1 110φ, manufactured by Advantec Co., Ltd.) that had been previously weighed was placed on the front side sheet at the position where the physiologic saline was administered. On the filter paper, a stainless cylindrical weight with a diameter of 110 mm was placed and held for 5 minutes. After completion of the test, the weight was removed, and the mass of the filter paper that absorbed the physiologic saline due to backflow was measured. The amount of backflow was calculated according to the following equation using the mass (mg) of the filter paper after the test and the mass (mg) of the filter paper before the test.

$$\text{Amount of backflow (mg)}=W1-W0$$

W1: mass (mg) of the filter paper after the test
W2: mass (mg) of the filter paper before the test Thirty minutes after the wight was removed, 20 ml of physiologic saline was again administered at the position where physiologic saline had been previously administered. The amount of backflow was measured using a newly prepared filter paper and the same wight holding time and method. The operations were repeated twice in total, and the amount of second backflow and the amount of third backflow were calculated. The amount of third backflow was defined as the amount of backflow after repeated use.

Lower amount of backflow means better anti-backflow properties. An amount of backflow of 60 mg or less is preferred because it provides prevention of backflow of a water-based liquid such as urine to the skin side even during wearing in a state after absorbing a water-based liquid such as urine, and thereby comfortability. Similarly, lower amount of backflow after repeated use also means better anti-backflow properties. An amount of backflow after repeated use of 1500 mg or less is preferred because it provides sustained comfortability even after repeated use.

(12) Surface Flow Distance in Inclined State

A front side sheet, an absorbent article, and a back side sheet were bonded together to form a substantially rectangular sanitary material product as a sample. The sample was fixed to a tilting table with an angle of inclination of 45° so that the longitudinal direction of the sample agrees with the direction of inclination. At this time, the sample was fixed in an extended state to eliminate wrinkles on the front side sheet. Then, a total of 25 g of 0.90% physiologic saline (colored with blue dye) previously prepared in a beaker was dropped at a position 1 cm below the top edge of the front side sheet with a microtube pump at a rate of 1.5 g/sec. Then, the following behavior will be observed: the physiologic saline flows down on the surface of the front side sheet in the inclined direction, is absorbed into the front side sheet at a certain position, and then disappears from the surface of the front side sheet. The distance from the drop position as the starting point to the disappearance of the physiologic saline is defined as the surface flow distance. The maximum surface flow distance observed during a drop of a total of 25 g of physiologic saline was defined as the surface flow distance in the inclined state.

Smaller surface flow distance means better anti-leakage properties. A sanitary material product with a surface flow distance of more than 45 mm was determined not to exhibit absorption properties at a practical level because of significant leakage when the sanitary material product was in an inclined state, such as when one wearing the sanitary material product is in a sleeping position.

(13) Absorption in Inclined State

In the method described in (12) above, an excess amount of a physiologic saline was dropped, and the drop of physiologic saline was continued until leakage of the physiologic saline from the lower end surface of the sanitary material product was observed. More specifically, 250 g of physiologic saline was prepared in a beaker, and the physiologic saline was dropped at the same dropping rate as in the method described in (12) above, and the dropping was stopped at the time when leakage of the physiologic saline from the lower end surface of the sanitary material product was observed. The mass (g) of the physiologic saline remaining in the beaker without being dropped was measured, and the absorption in the inclined state was calculated using the following equation.

Absorption in the inclined state (g)=250−$Q$ $Q$: mass (g) of the physiologic saline remaining in the beaker without being dropped Higher absorption in the inclined state means better anti-leakage properties. A sanitary material product with an absorption in the inclined state of less than 100 g was determined not to exhibit absorption properties at a practical level because of significant leakage when the sanitary material product was in an inclined state, such as when one wearing the sanitary material product is in a sleeping position.

(14) Particle Diameter of Water-Absorbing Polymer

A saucer, and sieves with nominal apertures of 106 μm, 212 μm, 300 μm, 425 μm, 500 μm, 1 mm (1000 μm), and 1.4 mm in accordance with JIS Z8801 were stacked in this order from the bottom. Thereafter, 5.00 g of the water-absorbing polymer were placed on a 1.7-mm sieve and shaken for 10 minutes using automated shaker (horizontal turn shaker SKH-01, manufactured by As One Corporation) with a memory setting of 3. Then, the presence and the mass of the water-absorbing polymer on the sieves and the saucer were determined. However, when the mass of the water-absorbing polymer present on the sieves or the saucer is less than 5% of 5.00 g that was the feed amount, then there shall be no water-absorbing polymer on the sieves or the saucer.

From the obtained results, the upper limit of the particle diameter of the water-absorbing polymer was considered as the sieve aperture that was one level larger than a sieve having the largest aperture of the sieves in which the presence of the water-absorbing polymer was found in an amount of 5% or more relative to 5.00 g of the preparation amount. For example, when the water-absorbing polymer is sieved, and as a result the sieve having the largest aperture of the sieves in which the presence of the water-absorbing polymer is found in an amount of 5% or more relative to 5.00 g of the preparation amount is one having an aperture of 425 μm, 500 μm that is the aperture one level larger than that of the sieve is considered as the upper limit of the particle diameter of the water-absorbing polymer, and thus the particle diameter of the water-absorbing polymer is 500 μm or less.

The lower limit of the particle diameter of the water-absorbing polymer was considered as the aperture of a sieve having the smallest aperture of the sieves in which the presence of the water-absorbing polymer was found in an amount of 5% or more relative to 5.00 g of the preparation amount. It is noted that an expression of a range does not include the indicated values. For example, a range of "more than 212 μm and 300 μm or less" is expressed as "212-300 (μm)" in tables. When the water-absorbing polymer passed through the sieve with an aperture of 106 and was also found on the saucer in an amount of 5% or more relative to 5.00 g of the preparation amount, then the saucer was considered as a sieve with an aperture of 0 For example, when the water-absorbing polymer is sieved, and as a result the sieve having the smallest aperture of the sieves in which the presence of the water-absorbing polymer is found in an amount of 5% or more relative to 5.00 g of the preparation amount is one having an aperture of 106 106 μm is considered as the lower limit of the particle diameter of the water-absorbing polymer, and thus the particle diameter of the water-absorbing polymer is more than 106 When the presence of the water-absorbing polymer was also found on the saucer in an amount of 5% or more relative to 5.00 g of the preparation amount, the lower limit as a measurement result is described as "the particle diameter of the water-absorbing polymer is more than 0 μm."

(Manufacturing Example 1: Nonwoven Fabric A)

A mass of short fibers (fiber diameter: 13 μm, fiber length: 51 mm, single fiber strength: 0.04 N) made of rayon (standard moisture regain: 11%) was opened with a carding machine and then made into a web a having a basis weight of 20 g/m² with a cross-lapped web forming machine. In addition, 70 mass % of the same mass of short fibers made of rayon as described above, and 30 mass % of a mass of hollow short fibers (fiber diameter: 30 μm, fiber length: 51 mm, single fiber strength: 0.27 N, porosity: 30%) made of polyethylene terephthalate (standard moisture regain:0.4%) were mixed and opened with a carding machine and then made into a web b having a basis weight of 20 g/m² with a cross-lapped web forming machine. The obtained web a and web b were stacked, then entangled each other by applying a high-pressure water stream from the side of the web a at a pressure of 3 MPa and a rate of 1.0 m/min, and dried at 150° C. for 3 minutes to obtain a nonwoven fabric A with a basis weight of 40 g/m². The surface on the web a-derived side of the nonwoven fabric A had openings with a 90% diameter of 114 μm and a difference between the 90% diameter and the 10% diameter of 91 The surface on the web b-derived side had openings with a porosity of 37%.

(Manufacturing Example 2: Nonwoven Fabric B)

Two sheets of the same web b as in Manufacturing Example 1 were stacked, entangled each other under the same conditions as Manufacturing Example 1, and dried to obtain a nonwoven fabric B with a basis weight of 40 g/m². One of the surfaces of the nonwoven fabric B which has smaller 90% diameter had openings with a 90% diameter of 205 μm and a difference between the 90% diameter and the 10% diameter of 159 The other surface had openings with a porosity of 38%.

(Manufacturing Example 3: Nonwoven Fabric C)

Two sheets of the same web a as in Manufacturing Example 1 were stacked, entangled each other under the same conditions as Manufacturing Example 1, and dried to obtain a nonwoven fabric C with a basis weight of 40 g/m². One of the surfaces of the nonwoven fabric C which has smaller 90% diameter had openings with a 90% diameter of 110 μm and a difference between the 90% diameter and the 10% diameter of 88 The other surface had openings with a porosity of 19%.

(Manufacturing Example 4: Nonwoven Fabric D)

As one of webs to be stacked, the same web a as in Manufacturing Example 1 was used. As the other of the webs, 70 mass % of the same mass of short fibers made of rayon as the web a, and a mass of solid short fibers (fiber diameter: 14 fiber length: 51 mm, single fiber strength: 0.11 N, porosity: 0%) made of polyethylene terephthalate (standard moisture regain: 0.4%) were mixed and opened with a carding machine and then made into a web $b_2$ of 20 g/m² with a cross-lapped web forming machine. The web a and web $b_2$ were stacked, then entangled each other under the same conditions as Manufacturing Example 1, and dried to obtain a nonwoven fabric D with a basis weight of 40 g/m². The surface on the web a-derived side of the nonwoven fabric D had openings with a 90% diameter of 109 μm and a difference between the 90% diameter and the 10% diameter of 84 The surface on the web $b_2$-derived side had openings with a porosity of 21%.

(Manufacturing Example 5: Nonwoven Fabric E)

A mass of solid short fibers (fiber diameter: 12 μm, fiber length: 51 mm, single fiber strength: 0.09 N, porosity: 0%) made of polyethylene terephthalate (standard moisture regain: 0.4%) was opened with a carding machine and then made into a web $a_2$ having a basis weight of 20 g/m² with a cross-lapped web forming machine. As the other web to be stacked, the same web b as in Manufacturing Example 1 was used. The web $a_2$ and web b were stacked, and entangled each other under the same conditions as Manufacturing Example 1. Thereafter, a hydrophilizing agent (a nonionic surfactant containing a hydrophilic polyester component) was added, followed by drying to obtain a nonwoven fabric E with a basis weight of 40 g/m². The surface on the web $a_2$-derived side of the nonwoven fabric E had openings with a 90% diameter of 125 μm and a difference between the 90% diameter and the 10% diameter of 98 The surface on the web b-derived side had openings with a porosity of 37%.

(Manufacturing Example 6: Nonwoven Fabric F)

A mass of short fibers (fiber diameter: 8 μm, fiber length: 51 mm, single fiber strength: 0.02 N) made of rayon (standard moisture regain: 11%) was opened with a carding machine and then made into a web $a_3$ having a basis weight of 20 g/m² with a cross-lapped web forming machine. As the other web to be stacked, the same web b as in Manufacturing Example 1 was used. The web $a_3$ and web b were stacked, then entangled each other under the same conditions as Manufacturing Example 1, and dried to obtain a nonwoven fabric F with a basis weight of 40 g/m². The surface on the web $a_3$-derived side of the nonwoven fabric F had openings with a 90% diameter of 98 μm and a difference between the 90% diameter and the 10% diameter of 77 The surface on the web b-derived side had openings with a porosity of 36%.

(Manufacturing Example 7: Nonwoven Fabric G)

As one of webs to be stacked, the same web a as in Manufacturing Example 1 was used. As the other of the webs, 70 mass % of a mass of short fibers (fiber diameter: 17 μm, fiber length: 51 mm, single fiber strength: 0.09 N) made of rayon, and 30 mass % of the same hollow short fibers made of polyethylene terephthalate as used in Manufacturing Example 1 were mixed and opened with a carding machine, and then made into a web $b_3$ of 20 g/m² with a cross-lapped web forming machine. The web a and web $b_3$ were stacked, then entangled each other under the same conditions as Manufacturing Example 1, and dried to obtain a nonwoven fabric G with a basis weight of 40 g/m². The surface on the web a-derived side of the nonwoven fabric G had openings with a 90% diameter of 110 μm and a difference between the 90% diameter and the 10% diameter of 93 The surface on the web $b_3$-derived side had openings with a porosity of 42%.

(Manufacturing Example 8: Nonwoven Fabric H)

As one of webs to be stacked, the same web a as in Manufacturing Example 1 was used. As the other of the webs, 50 mass % of the same mass of short fibers made of rayon as used in Manufacturing Example 1, and 50 mass % of the same hollow short fibers made of polyethylene terephthalate as used in Manufacturing Example 1 were mixed and opened with a carding machine, and then made into a web $b_4$ having a basis weight of 20 g/m² with a cross-lapped web forming machine. The web a and web $b_4$ were stacked, then entangled each other under the same conditions as Manufacturing Example 1, and dried to obtain a nonwoven fabric H with a basis weight of 40 g/m². The surface on the web a-derived side of the nonwoven fabric H had openings with a 90% diameter of 118 μm and a difference between the 90% diameter and the 10% diameter of 88 The surface on the web $b_4$-derived side had openings with a porosity of 46%.

(Manufacturing Example 9: Nonwoven Fabric I)

Two sheets of the same web $a_3$ as used in Manufacturing Example 6 were stacked, entangled each other under the same conditions as Manufacturing Example 1, and dried to obtain a nonwoven fabric I of 40 g/m².

Example 1

Commercially available water-absorbing polymers (IM930 manufactured by SDP Global Co., Ltd.) were classified using sieves with apertures of 300 μm and 212 μm to obtain a water-absorbing polymer A with a particle diameter of more than 212 μm and 300 μm or less. Thereafter, using the nonwoven fabric A as a first nonwoven fabric, and considering the surface of the nonwoven fabric A on the web a-derived side as a first a surface, a styrene hot melt adhesive was sprayed onto the first a surface at 1 g/m², onto which the water-absorbing polymer A was further uniformly sprayed at 300 g/m². Then, using another nonwoven fabric A as a second nonwoven fabric, and similarly considering the surface on the web a-derived side as a surface of the second nonwoven fabric on the water-absorbing polymer side (second a surface), a styrene hot melt adhesive was sprayed onto the second a surface at 1 g/m², and then the surface coated with the hot melt adhesive of the second nonwoven fabric is allowed to cover and be in contact with the water-absorbing polymer sprayed onto the first nonwoven fabric, followed by fixation by applying pressure to obtain an absorbent article. The absorbent article was cut int a substantial rectangle of 30 cm×10 cm. In addition, a thermal bond dry nonwoven fabric prepared using a composite short fiber having a sheath-core structure containing polyethylene in the core portion and polypropylene in the sheath portion was cut into a substantial rectangle of 35 cm×14 cm as a front side sheet. Then, a styrene hot melt adhesive was sprayed onto the front side sheet at 1 g/m², which was then superimposed on the first b surface and fixed by applying pressure. In addition, using a porous polyethylene film and a spunbonded dry nonwoven fabric made of polypropylene cut into a 35 cm×20 cm substantial rectangle as a back side sheet, a styrene hot melt adhesive was sprayed onto the back side sheet at 1 g/m², which was then superimposed on the surface of the second nonwoven fabric on the opposite side of the water-absorbing polymer (second b surface) and fixed by applying pressure. At this time, the rectangular front side sheet, absorbent article, and back side sheet materials are stacked and fixed by applying pressure such that the longitudinal directions of them with rectangular shapes are aligned while their centers of gravity are coincident, thereby obtaining a sanitary material product. Table 1 shows the compositions of and evaluation results from the obtained absorbent article and sanitary material product.

Examples 2 to 4, Comparative Examples 1 to 5

Absorbent articles and sanitary material products were obtained in the same manner as in Example 1, except that first nonwoven fabrics and second nonwoven fabrics described in tables 1 and 2, respectively, were used. Tables 1 and 2 show the evaluation results from the obtained absorbent articles and sanitary material products. In Comparative Examples 1 and 2, since the nonwoven fabrics B and C were monolayer and had no difference in the compositions of the front and back surfaces, the both surfaces were analyzed for 90% opening diameter, and a surface with smaller 90% opening diameter was positioned on the side of the water-absorbing polymer.

TABLE 1

|  |  |  | Example 1 | Example 2 | Example 3 | Example 4 |
|---|---|---|---|---|---|---|
| First nonwoven fabric | Type | — | A | F | G | H |
|  | 90% diameter of openings in first a surface | μm | 114 | 98 | 110 | 118 |
|  | Difference between the 90% diameter and the 10% diameter of openings in first a surface | μm | 91 | 77 | 93 | 88 |
|  | Porosity of openings in first b surface | % | 37 | 36 | 42 | 46 |
|  | Water holding rate | % | 1383 | 1396 | 1372 | 1013 |
| Second nonwoven fabric | Type | — | A | F | A | A |
|  | 90% diameter of openings in second a surface | μm | 114 | 98 | 114 | 114 |
|  | Difference between the 90% diameter and the 10% diameter of openings in second a surface | μm | 91 | 77 | 91 | 91 |
| Third nonwoven fabric | Type | — | — | — | — | — |
|  | Water absorption height in Byreck's test | mm | — | — | — | — |
| Water-absorbing polymer group | Particle diameter | μm | 212-300 | 212-300 | 212-300 | 212-300 |
| Absorbent article | Loss of water-absorbing polymer | g/m$^2$ | 0.7 | 0.0 | 0.8 | 0.8 |
|  | Thickness | mm | 2.1 | 2.0 | 2.4 | 2.5 |
| Sanitary material product | Absorption in inclined state | g | 182 | 184 | 191 | 173 |
|  | Surface flow distance in inclined state | Mm | 35 | 34 | 29 | 38 |
|  | Backflow | mg | 31 | 36 | 33 | 45 |
|  | Backflow after repeated use | mg | 1035 | 992 | 1157 | 1332 |

TABLE 2

|  |  |  | Comparative Example 1 | Comparative Example 2 | Comparative Example 3 | Comparative Example 4 | Comparatove Example 5 |
|---|---|---|---|---|---|---|---|
| First nonwoven fabric | Ttype | — | B | C | D | E | A |
|  | 90% diameter of openings in first a surface | μm | 205 | 110 | 109 | 125 | 114 |
|  | Difference between the 90% diameter and the 10% diameter of openings in first a surface | μm | 159 | 88 | 84 | 98 | 91 |
|  | porosity of openings in first b surface | % | 38 | 19 | 21 | 37 | 37 |
|  | Water holding rate | % | 1550 | 1136 | 1319 | 724 | 1383 |

TABLE 2-continued

|  |  |  | Comparative Example 1 | Comparative Example 2 | Comparative Example 3 | Comparative Example 4 | Comparatove Example 5 |
| --- | --- | --- | --- | --- | --- | --- | --- |
| Second nonwoven fabric | Type | — | A | A | A | A | B |
|  | 90% diameter of openings in second a surface | μm | 114 | 114 | 114 | 114 | 200 |
|  | Difference between the 90% diameter and the 10% diameter of openings in second a surface | μm | 91 | 91 | 91 | 91 | 161 |
| Third nonwoven fabric | Type | — | — | — | — | — | — |
|  | Water absorption height in Byreck's test | mm | — | — | — | — | — |
| Water-absorbing polymer group | Particle diameter | μm | 212-300 | 212-300 | 212-300 | 212-300 | 212-300 |
| Absorbent article | Loss of water-absorbing polymer | g/m² | 13.2 | 0.3 | 0.3 | 0.9 | 13.2 |
|  | Thickness | mm | 2.3 | 1.8 | 2.0 | 2.2 | 2.2 |
| Sanitary material product | Aabsorption in inclined state | g | 185 | 152 | 121 | 188 | 183 |
|  | Surface flow distance in inclined state | mm | 33 | 47 | 80 | 38 | 35 |
|  | Backflow | mg | 25 | 65 | 39 | 41 | 33 |
|  | Backflow after repeated use | mg | 1121 | 953 | 1209 | 1925 | 998 |

Comparison of Example 1 to Comparative Examples 1 and 5 demonstrates that the 90% diameter and the difference between the 90% diameter and the 10% diameter of the first a surface and the second a surface of the first nonwoven fabric that satisfy the ranges of the present invention result in excellent prevention of loss of the water-absorbing polymers. Further comparison of Example 1 to Example 2 demonstrates that the 90% diameter and the difference between the 90% diameter and the 10% diameter of the first a surface and the second a surface that are within the preferred ranges of the present invention enable reduction of the loss amount.

Comparison of Example 1 to Comparative Examples 2 and 3 demonstrates that the first b surface of the first nonwoven fabric that satisfies the range of the porosity defined in the present invention enables smaller surface flow distance. As a result, the sanitary material product has superior absorption because it is capable of absorption from more upstream in an inclined state.

Comparison of Example 1 to Example 3 demonstrates that the porosity of the first b surface of the first nonwoven fabric that is within the preferred range of the present invention can provide better absorption.

Comparison of Example 1 to Comparative Example 4 demonstrates that the water holding rate of the first nonwoven fabric that is within the range defined in the present invention enables keeping hydrophilic, resulting in excellent anti-reversing properties in repeated use.

Example 5

An absorbent article and a sanitary material product were obtained in the same manner as in Example 1, except that the sieves used for classification of water-absorbing polymers had apertures of 1000 μm and 106 μm, and a water-absorbing polymer B with a particle diameter of more than 106 μm and 1000 μm or less was used in Example 1. Table 3 shows the evaluation results from the absorbent article and sanitary material product.

Example 6

An absorbent article and a sanitary material product were obtained in the same manner as in Example 1, except that the sieves used for classification of water-absorbing polymers had apertures of 212 μm and 106 μm, and a water-absorbing polymer C with a particle diameter of more than 106 μm and 212 μm or less was used in Example 1. Table 3 shows the evaluation results from the obtained absorbent article and sanitary material product.

Comparative Example 6

An absorbent article and a sanitary material product were obtained in the same manner as in Example 1, except that the sieve used for classification of water-absorbing polymers had an aperture of 106 and a water-absorbing polymer D with a particle diameter of more than 0 μm and 106 μm or less was used in Example 1. Table 3 shows the evaluation results from the obtained absorbent article and sanitary material product.

$g/m^2$, and then the surface coated with the hot melt adhesive of the third nonwoven fabric was allowed to cover and be in contact with the water-absorbing polymer. Further, a styrene hot melt adhesive was sprayed onto the other surface of the nonwoven fabric C at 1 $g/m^2$, onto which the water-absorbing polymer A was further uniformly sprayed at 150 $g/m^2$.

TABLE 3

|  |  |  | Example 5 | Example 6 | Comparatove Example 6 |
|---|---|---|---|---|---|
| First nonwoven fabric | Type | — | A | F | A |
|  | 90% diameter of openings in first a surface | μm | 114 | 98 | 114 |
|  | Difference between the 90% diameter and the 10% diameter of openings in first a surface | μm | 91 | 77 | 91 |
|  | Porosity of openings in first b surface | % | 37 | 36 | 37 |
|  | Water holding rate | % | 1383 | 1396 | 1383 |
| Second nonwoven fabric | Type | — | A | F | A |
|  | 90% diameter of openings in second a surface | μm | 114 | 98 | 114 |
|  | Difference between the 90% diameter and the 10% diameter of openings in second a surface | μm | 91 | 77 | 91 |
| Third nonwoven fabric | Type | — | — | — | — |
|  | Water absorption height in Byreck's test | mm | — | — | — |
| Water-absorbing polymer group | Particle diameter | μm | 106-1000 | 106-212 | 0-106 |
| absorbent article | Loss of water-absorbing polymer | $g/m^2$ | 0.2 | 0.5 | 46 |
|  | Thickness | mm | 2.1 | 2.0 | 2.1 |
| Sanitary material product | Absorption in inclined state | g | 109 | 231 | 88 |
|  | Surface flow distance in inclined state | mm | 35 | 34 | 35 |
|  | Backflow | mg | 42 | 28 | 1922 |
|  | Backflow after repeated use | mg | 1067 | 1001 | 1957 |

Comparison of Example 1 to Comparative Example 6 demonstrates that the particle diameters of the water-absorbing polymers that are within the range defined in the present invention enable prevention of loss of the water-absorbing polymers while providing high absorption.

Comparison of Example 1 to Example 6 demonstrates that the 90% diameter and the difference between the 90% diameter and the 10% diameter of the first a surface and the second a surface that are within the ranges of the present invention and use of finer water-absorbing polymers can provide high absorption.

Example 7

Using the nonwoven fabric A as a first nonwoven fabric, and considering the surface of the nonwoven fabric A on the web a-derived side as a first a surface, a styrene hot melt adhesive was sprayed onto the first a surface at 1 $g/m^2$, onto which the water-absorbing polymer A was further uniformly sprayed at 150 $g/m^2$. Then, using the nonwoven fabric C as a third nonwoven fabric, a styrene hot melt adhesive was sprayed onto one surface of the nonwoven fabric C at 1

Then, using another nonwoven fabric A as a second nonwoven fabric, a styrene hot melt adhesive was sprayed onto the surface on the web a-derived side at 1 $g/m^2$, and then the surface coated with the hot melt adhesive of the second nonwoven fabric was allowed to cover and be in contact with the water-absorbing polymer sprayed onto the third nonwoven fabric, followed by fixation by applying pressure to obtain an absorbent article. Thereafter, a sanitary material product was obtained in the same manner as in Example 1. Table 4 shows the evaluation results from the obtained absorbent article and sanitary material product.

Examples 8 and 9

An absorbent article and a sanitary material product were obtained as in Example 6, except that a nonwoven fabric I or a nonwoven fabric B was used as the third nonwoven fabric instead of the nonwoven fabric C in Example 7. Table 4 shows the evaluation results from the obtained absorbent article and sanitary material product.

TABLE 4

|  |  |  | Example 7 | Example 8 | Example 9 |
|---|---|---|---|---|---|
| First nonwoven fabric | Type | — | A | A | A |
|  | 90% diameter of openings in first a surface | μm | 114 | 114 | 114 |
|  | Difference between the 90% diameter and the 10% diameter of openings in first a surface | μm | 91 | 91 | 91 |
|  | Porosity of openings in first b surface | % | 37 | 37 | 37 |
|  | Water holding rate | % | 1383 | 1383 | 1383 |
| Second nonwoven fabric | Type | — | A | A | A |
|  | 90% diameter of openings in second a surface | μm | 114 | 114 | 114 |
|  | Difference between the 90% diameter and the 10% diameter of openings in second a surface | μm | 91 | 91 | 91 |
| Third nonwoven fabric | Type | — | C | I | B |
|  | Water absorption height in Byreck's test | mm | 121 | 152 | 10 |
| Water-absorbing polymer group | Particle diameter | μm | 212-300 | 212-300 | 212-300 |
| Absorbent article | Loss of water-absorbing polymer | g/m² | 0.4 | 0.2 | 0.2 |
|  | Thickness | mm | 2.6 | 2.6 | 2.6 |
| Sanitary material product | Absorption in inclined state | g | 202 | 215 | 215 |
|  | Surface flow distance in inclined state | mm | 35 | 35 | 35 |
|  | Backflow | mg | 32 | 36 | 36 |
|  | Backflow after repeated use | mg | 211 | 83 | 996 |

Comparison of Example 1 to Examples 7 and 8 demonstrates that use of a nonwoven fabric as a third nonwoven fabric, that shows a water absorption height within the preferred range of the present application in a Byreck's test, enables excellent anti-reversing properties during repeated use.

Example 10

The nonwoven fabric A was used as a core wrap sheet comprising a first nonwoven fabric and a second nonwoven fabric connected together. The nonwoven fabric A was cut into a substantial rectangle with a long side of 30 cm and a short side of 20 cm. Considering the surface of the nonwoven fabric A on the web a-derived side as a first a surface, a styrene hot melt adhesive was sprayed onto the first a surface at 1 g/m², onto which the water-absorbing polymer A was further uniformly sprayed at 150 g/m². Then, the nonwoven fabric A was folded so that a pair of the long sides of the nonwoven fabric A overlap on the center line obtained by connecting the midpoints of a pair of the short sides of the nonwoven fabric A. This resulted in a structure where the water-absorbing polymers A were enclosed with the nonwoven fabric A, which was fixed by applying pressure to obtain a 30 cm×10 cm substantially rectangular absorbent article. Thereafter, a sanitary material product was obtained in the same manner as in Example 1. Table 5 shows the evaluation results from the obtained absorbent article and sanitary material product.

Example 11

The nonwoven fabric A was used as a core wrap sheet comprising a first nonwoven fabric and a second nonwoven fabric connected together. The nonwoven fabric A was cut into a substantial rectangle with a long side of 30 cm and a short side of 20 cm. Considering the surface of the nonwoven fabric A on the web a-derived side as a first a surface, a styrene hot melt adhesive was sprayed onto the first a surface at 1 g/m², onto which the water-absorbing polymer A was further uniformly sprayed at 150 g/m². Then, the nonwoven fabric C as a third nonwoven fabric, prepared by cutting the non-woven fabric C into 30 cm long side×10 cm short side, and a styrene hot melt adhesive was sprayed onto one surface of the nonwoven fabric C at 1 g/m². The surface coated with the hot melt adhesive of the third nonwoven fabric was allowed to cover and be in contact with the water-absorbing polymers such that the center line of the nonwoven fabric A and the center line of the third nonwoven fabric overlap. Thereafter, an absorbent article and a sanitary material product were obtained in the same manner as in Example 10. Table 5 shows the evaluation results from the obtained absorbent article and sanitary material product.

TABLE 5

|  |  |  | Example 10 | Example 11 |
|---|---|---|---|---|
| Core wrap sheet nonwoven fabric | Type |  | A | A |
|  | 90% diameter of openings in first a surface | μm | 114 | 114 |
|  | Difference between the 90% diameter and the 10% diameter of openings in first a surface | μm | 91 | 91 |
|  | Porosity of openings in first b surface | % | 37 | 37 |
|  | Water holding rate | % | 1383 | 1383 |
| Third nonwoven fabric | Type |  | — | C |
|  | Water absorption height in Byreck's test | mm | — | 121 |
| Water-absorbing polymer group | Particle diameter | μm | 212-300 | 212-300 |
| Absorbent article | Loss of water-absorbing polymer | g/m$^2$ | 0.3 | 0.3 |
|  | Thickness | mm | 2.2 | 2.6 |
| Sanitary material product | Absorption in inclined state | g | 191 | 213 |
|  | Surface flow distance in inclined state | mm | 35 | 33 |
|  | Backflow | mg | 28 | 32 |
|  | Backflow after repeated use | mg | 981 | 186 |

INDUSTRIAL APPLICABILITY

The absorbent article of the present invention shows excellent prevention of loss of water-absorbing polymers and excellent absorption properties, and can be suitably used as various sanitary material products, such as tape-type paper diapers, pants-type paper diapers, sanitary napkins, and urine collecting pads.

REFERENCE SIGNS LIST first nonwoven fabric
1a the surface of the first nonwoven fabric on the side of the water-absorbing polymer group
1b the surface of the first nonwoven fabric on the opposite side of the water-absorbing polymer group
2 second nonwoven fabric
3 third nonwoven fabric
4 core wrap sheet
4a the surface of the core wrap sheet on the side of the water-absorbing polymer group
4b the surface of the core wrap sheet on the opposite side of the water-absorbing polymer group
5 water-absorbing polymer group
5a first water-absorbing polymer group
5b second water-absorbing polymer group
6 covering material
7 absorbent article
8 front side sheet
9 back side sheet
10 sanitary material product
c position at which the cross section of the absorbent article is observed

The invention claimed is:

1. An absorbent article comprising a first nonwoven fabric and a second nonwoven fabric that sandwich a water-absorbing polymer group,
   wherein the surface of the first nonwoven fabric on the side of the water-absorbing polymer group has openings,
   wherein the 90% diameter in the diameter distribution of the openings is 10 μm or more and 130 μm or less,
   wherein the difference between the 90% diameter and the 10% diameter in the diameter distribution of the openings is 100 μm or less;
   wherein the surface of the first nonwoven fabric on the opposite side of the water-absorbing polymer group has openings,
   wherein the porosity of the openings is 25% or more and 50% or less;
   wherein the water holding rate of the first nonwoven fabric is 1000 mass % or more;
   wherein at least one surface of the second nonwoven fabric has openings,
   wherein the 90% diameter in the diameter distribution of the openings is 10 μm or more and 130 μm or less,
   wherein the difference between the 90% diameter and the 10% diameter in the diameter distribution of the openings is 100 μm or less;
   wherein the water-absorbing polymer constituting the water-absorbing polymer group is particulate; and
   wherein the particle diameter of the water-absorbing polymer is more than 106 μm and 1000 μm or less.

2. The absorbent article according to claim 1,
   wherein the water-absorbing polymer group comprises two layers of water-absorbing polymer groups; and
   wherein the absorbent article further comprises a third nonwoven fabric sandwiched between the two layers of water-absorbing polymer groups.

3. The absorbent article according to claim 1, wherein the first nonwoven fabric and the second nonwoven fabric are connected together to form a core wrap sheet.

4. The absorbent article according to claim 1, wherein the particle diameter of the water-absorbing polymer is more than 106 μm and 300 μm or less.

5. A sanitary material product, comprising an absorbent article according to claim 1.

* * * * *